United States Patent [19]

Kinugasa et al.

[11] 4,045,450

[45] Aug. 30, 1977

[54] OPTICAL RESOLUTION OF DL-PANTOLACTONE

[75] Inventors: Akikazu Kinugasa, Takayama; Toshio Okuda, Gifu; Makoto Goto, Takayama; Mitsuo Saito, Tono, all of Japan

[73] Assignee: Alps Pharmaceutical Ind. Co., Ltd., Mukai, Japan

[21] Appl. No.: 657,660

[22] Filed: Feb. 12, 1976

[30] Foreign Application Priority Data

Feb. 19, 1975 Japan .................................. 50-21330

[51] Int. Cl.$^2$ ........................................ C07D 307/83
[52] U.S. Cl. ............................. 260/343.6; 260/570.6
[58] Field of Search ........................................ 260/343.6

[56] References Cited

U.S. PATENT DOCUMENTS

| 2,460,239 | 1/1949 | Pickel et al. .......................... 260/344 |
| 2,460,240 | 1/1949 | Pickel et al. .......................... 260/344 |

Primary Examiner—Cecilia M. S. Jaisle
Attorney, Agent, or Firm—Jones, Tullar & Cooper

[57] ABSTRACT

The optical resolution of DL-pantolactone is effected by reacting DL-pantolactone or its alkali salt derived therefrom, respectively, with an optically active N-substituted aminophenylpropanol of the general formula:

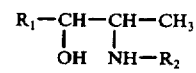

wherein $R_1$ is a phenyl group which may be substituted and $R_2$ is an aralkyl group in which the benzene ring may bear a substituent, or its mineral acid addition salt; separating the resulting diastereomers by the aid of difference in their dissolubility; and decomposing them to give the corresponding optical antipodes. This method can provide the antipodes in high purity and yield and can be carried out with ease.

13 Claims, No Drawings

OPTICAL RESOLUTION OF DL-PANTOLACTONE

The present invention relates to the optical resolution of DL-pantolactone and, more particularly, to a method of optically resolving DL-pantolactone using an optically active N-substituted aminophenylpropanol.

The optically active antipode of DL-pantolactone or D-pantolactone is useful as an intermediate for preparing D-pantothenic acid which possesses a physiologically active property. The L-pantolactone, on the other hand, is employed, after being racemized, as a starting material for racemic resolution and it is useful as an optically active resolving agent for dl-basic compounds. Pantolactone which is obtainable by chemical synthesis is generally in the form of racemate so that its antipodes are obtained by the racemic resolution method.

Many attempts have heretofore been made to optically resolving DL-pantolactone using a variety of optically active resolving agents. For example, there are disclosed quinine in U.S. Pat. No. 2,319,545; brucine in U.S. Pat. Nos. 2,474,719 and 3,009,922; ephedrine in U.S. Pat. Nos. 2,460,239 and 2,460,240 and Czechoslovak Pat. No. 88,066; 1-p-nitrophenyl-2-amino-1,3-propanediol in Pat. No. 37,505 of Democratic Republic of Germany and Japanese Patent Publication No. 9,176/1966; L-amino acids in Japanese Patent Publication No. 12,149/1968; dehydroabiethylamine in Canadian Patent No. 770,177; and d-alpha-threonamine in U.S.S.R. Pat. No. 201,426. These known agents, however, cannot give a high optical yield and have disadvantages in industrial application and economy because they ar expensive and their procedures are complicated.

It is therefore an object of the present invention to provide a method by which DL-pentolactone is optically resolved easily and efficiently on an industrial scale. Other objects, advantages and features of the present invention will become apparent in the following description of the specification and from the appended claims.

The method of the present invention involves reacting DL-pantolactone or its alkali salt derived therefrom, respectively, with an optically active N-substituted aminophenylpropanol of the general formula:

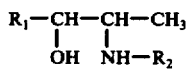

wherein $R_1$ is a phenyl group which may be substituted and $R_2$ is an aralkyl group in which the benzene ring may bear a substituent, or its mineral acid addition salt; separating the resulting diastereomers by the aid of difference in their dissolubility; and decomposing them to give the corresponding optical antipodes. The phenyl group in the $R_1$ group may be substituted by a halogen atom such as chlorine, an aliphatic lower alkyl group having from 1 to 4 carbon atoms such as methyl or ethyl and/or an aliphatic lower alkoxy group in which the alkyl group is the same as above. The aralkyl group in the $R_2$ group may be an aralkyl having from 7 to 10 carbon atoms such as benzyl, phenethyl, phenylpropyl or alpha-methylbenzyl in which the phenyl group may be substituted by a halogen atom such as chlorine, an aliphatic lower alkyl group such as methyl or ethyl and/or an aliphatic lower alkoxy group having the same alkyl group as above. The optically active N-substituted aminophenylpropanol may also be employed in the form of an acid addition salts. For this purpose, the acid addition salt may be prepared in conventional manner using a mineral acid such as hydrochloric or sulfuric acid.

In the practice of the method according to the present invention, the diastereomers corresponding to the D- and L-pantolactone can be obtained in both cases where an alkali salt of DL-pantoic acid is treated with a mineral acid addition salt of an optically active N-substituted aminophenylpropanol and where DL-pantolactone is treated with feee, optically active N-substituted aminophenylpropanol. The alkali salt of DL-pantoic acid is obtainable by treating the DL-pantolactone with an alkali, such as alkali metal hydroxide, e.g., sodium or potassium hydroxide to split off its lactone ring and then neutralizing excess alkali with a mineral acid, such as hydrochloric or sulfuric acid. Where d-N-substituted aminophenylpropanol of its mineral acid addition salt is employed as the resolving agent, D-pantoic acid d-N-substituted aminophenylpropanol salt is formed as the sparingly soluble diastereomer, and L-pantoic acid d-N-substituted aminophenylpropanol salt is produced as the easily soluble one. Where 1-N-substituted aminophenylpropanol or its mineral acid addition salt is used as the resolving agent, L-pantoic acid 1-N-substituted aminophenylpropanol is the sparingly soluble diastereomer and D-pantoic acid 1-N-substituted aminophenylpropanol salt is the easily soluble diastereomer. Since the sparingly soluble diastereomer and the corresponding easily soluble one exhibit a difference in dissolubility between each other to a great extent, one diastereomer can be isolated as pure crystals from the other. Accordingly, this procedure can avoid the recrystallization step which otherwise is needed for the complicated separation of the sparingly soluble diastereomer and can provide the sparingly solube diastereomer with efficacy from an industrial point of view and in high yields and with high purity.

The amount of the optically active resolving agent can be reduced to about half mole stoichiometrically with respect to the compound to be optically resolved. In this case, no formation of any undesired material is recognized.

A solvent in which the diastereomers are formed and from which they are separated is usually water or an aqueous solution containing an organic solvent such as an aliphatic lower alcohol, e.g., methanol, ethanol or isopropanol and/or an aliphatic lower ketone, e.g., acetone. However, water is preferred from the economic standpoint.

The disasteromers obtained by said procedure may be easily decomposed with an alkali such as an alkali metal hydroxide, e.g., sodium or potassium hydroxide or a mineral acid such as hydrochloric acid or sulfuric acid. The sparingly soluble diastereomer is treated first with said alkali and then with a solvent incompatible with water such as benzene or ether. The resulting phase is heated with a mineral acid such as hydrochloric or sulfuric acid and then extracted with an organic solvent such as chloroform or ether, thereby causing the formation of the optically active pantolactone. The motor liquor from which the sparingly soluble diastereomer was separated is further treated with said alkali and then in substantially the same manner as described above to give the corresponding optically active pantolactone. Where a mineral acid is employed, substantially the same procedures as with said alkali may be taken.

The method of the present invention has the advantages from the industrial point of view in that DL-pantolactone can be converted into its optical antipodes in high purity and yields, the recrystallization of sparingly soluble diastereomers which are otherwise very complicated is not needed and the optically active resolving agent to be used is not subject to denaturation and can be so recovered almost quantitatively that the optical resolution can be effected in a stable and continuous manner.

The following examples serve to illustrate the present invention but they should not be construed as limiting the same thereto. In the following Examples, the optical rotation is expressed as $[\alpha]_D$.

EXAMPLE 1

A solution of 2.60 g. (0.2 mole) of DL-pantolactone in 50 ml. of water containing 8.2 g. of sodium hydroxide was adjusted to pH 7.2 with a 10% hydrochloric acid solution. To this mixture was added a solution of 33.3 g. (0.12 mole) of d-N-benzylphenylpropanolamine hydrochloride in 200 ml. of water which had been heated on a water bath to dissolve the hydrochloride therein. The resulting mixture was cooled, thereby precipitating out crystals which were then filtered and washed with water to give 38.4 g. (yield, 98.6%) of crystalline D-pantoic acid d-N-benzylphenylpropanolamine having an optical rotation of +17.8° in methanol.

A solution of 3.63 g. of said crystals in 45 ml. of a 10% sodium hydroxide aqueous solution was washed three times with 50 ml. of benzene. To the aqueous layer was added 20 ml. of concentrated hydrochloric acid, and the mixture was heated for 30 minutes at 80° C. on a water bath. The mixture cooled and extracted continuously overnight with chloroform. The chloroform layer was then dried over anhydrous sodium sulfate and the removal of the solvent gave 11.0 g. (yield, 89.5%) of D-pantolactone as crystals having an optical rotation in water of −49.8° and a melting point of 89° to 90° C.

b. The mother liquor from which D-pantoic acid d-N-benzylphenylpropanolamine had been separated was combined with said water washing, and the water was removed under reduced pressure therefrom. The resulting residue was dissolved 55 ml. of a 10% sodium hydroxide aqueous solution and washed three times with 50 ml. of benzene. The aqueous layer was mixed with 30 ml. of concentrated hydrochloric acid and heated for 30 minutes at 80° C. on a water bath. After the mixture was cooled, it was extracted with chloroform continuously overnight. The organic phase was dried over anhydrous sodium sulfate and the removal of the solvent therefrom left the residue which was in turn recrystallized from a trichlene-ligroin mixture, thereby giving 11.4 g. (yield, 87.8%) of L-pantolactone as crystals having an optical rotation in water of +50.0° and a melting point of 89° to 90° C.

c. All of said benzene phases were combined and, after the removal of the solvent and the adjustment to pH 5.2 with a 5% hydrochloric acid solution, the water was distilled off under reduced pressure to give 33.2 g. (recovery, 99.7%) of d-N-benzylphenylpropanolamine hydrochloride having an optical rotation in methanol of +10.6° and a melting point of 201° C.

EXAMPLE 2 a. The procedure of Example 1 was repeated except for using 33.3 g. of 1-N-benzylphenylpropanolamine hydrochloride, thereby giving 38.4 g. (yield, 98.6%) of L-pantoic acid 1-N-benzylphenylpropanolamine as crystals having an optical rotation of −17.8° in methanol.

With 36.3 g. of said crystals and the procedure of Example 1(a) above, L-pantolactone was produced with yield of 10.9 g. (88.7%) as crystals having an optical rotation in water of +49.3° and a melting point of 89° to 90° C.

b. With the procedure of Example 1(b) above, the mother liquid from which the L-pantoic acid 1-N-benzylphenylamine had been separated was treated to give 11.3 g. (yield, 86.9%) of D-pantolactone having an optical rotation in water of −49.7° and a melting point of 89° to 90° C.

c. By following the procedure of Example 1(c), said benzene phases gave 33.3 g. (recovery, 100%) of 1-N-benzylphenylpropanolamine hydrochloride having an optical rotation in methanol of −10.6° and a melting point of 201° C.

EXAMPLE 3 a. A mixture of 26.0 g. (0.2 mole) of DL-pantolactone, 28.9 g. (0.12 mole) of d-N-benzylphenylpropanolamine and 250 ml. of water was heated for 2 hours on a boiling water bath while being stirred and cooled to form a precipitate which was in turn filtratered and washed with water. This gave 37.6 g. (yield, 96.5%) of D-pantoic acid d-N-benzylphenylpropanolamine as crystals having an optical rotation of +17.8° in methanol.

A solution of 35.3 g. of said crystals in 45 ml. of a 10% sodium hydroxide aqueous solution was washed three times with 50 ml. of benzene. After the addition of 20 ml. of concentrated hydrochloric acid to the aqueous layer, the mixture was heated for 30 minutes at 80° C. on a water bath. The cooled mixture was then extracted with chloroform continuously overnight and the chloroform phase was dried over anhydrous sodium sulfate. The removal of the chloroform therefrom gave 10.7 g. (yield, 87.7%) of D-pantolactone as crystals which had an optical rotation in water of −49.7° and a melting point of 89° to 90° C.

b. The mother liquor from which said crystals had been separated and said water washing were combined and treated under reduced pressure to distil off the water. The resulting residue was dissolved in 55 ml. of a 10% sodium hydroxide aqueous solution and washed three times with 50 ml. of benzene. The aqueous layer was then mixed with 30 ml. of concentrated hydrochloric acid and heated for 30 minutes at 80° C. on a water bath. After being cooled, the mixture was extracted with chloroform continuously overnight. The chloroform phase was dried over anhydrous sodium sulfate, and the removal of the chloroform and recrystallization from a benzene-ligroin mixture gave 11.1 g. (yield, 85.4%) of L-pantolactone as crystals having an optical rotation in water of +50.1° and a melting point of 89° to 90° C.

EXAMPLE 4 a. A solution of 26.0 g. (0.2 mole) of DL-pantolactone in 50 ml. of an aqueous solution containing 11.5 g. of potassium hydroxide was mixed with a solution which was obtained by adding 49.2 g. (0.16 mole) of d-N-p-methoxybenzylphenylpropanolamine hydrochloride to 200 ml. of water which was previously adjusted to pH 7.2 with a 10% hydrochloric acid solution and then by heating the mixture on a water bath to dissolve the hydrochloride in water. After being cooled, the mixture was filtered to collect the crystalline material which was in turn washed with water to give 41.8 g. (yield, 99.7%) of D-pantoic acid d-N-p-methoxybenzylphenylpropanolamine as crystals having an optical rotation of +10.8° in methanol.

A solution of 39.5 g. of said crystals in 55 ml. of a 10% potassium hydroxide aqueous solution was washed three times with 80 ml. of ether. The aqueous layer was mixed with 20 ml. of concentrated hydrochloric acid and heated for 30 minutes at 80° C. on a water bath. After being cooled, the mixture was extracted with chloroform continuously overnight and the chloroform phase was dried over anhydrous sodium sulfate. The removal of the solvent from said chloroform phase gave 11.0 g. (yield, 89.5%) of D-pantolactone having an optical rotation in water of −49.8° and a melting point of 89° to 90° C.

b. The liquid from which said amine salt of D-pantoic acid had been separated and said water washing were combined. The water was removed from the combined solution under reduced pressure, leaving the residue to which 65 ml. of a 10% potassium hydroxide aqueous solution was added. After being washed three times with 80 ml. of ether, the aqueous phase was mixed with 30 ml. of concentrated hydrochloric acid and heated for 30 minutes at 80° C. After being cooled, the resulting solution was then extracted with chloroform continuously overnight and the extract was dried over anhydrous sodium sulfate. The chloroform was distilled off and the residue was recrystallized from a benzene-ligroin mixture to give 11.3 g. (yield, 86.9%) of L-pantolactone as crystals which had an optical rotation in water of +50.0° and a melting point of 89° to 90° C.

c. All of said ether phases were combined and treated to distil off the solvent. After the residue was adjusted to pH 5.2 with a 5% hydrochloric acid solution, the solution was concentrated to dryness under reduced pressure, thereby giving 48.8 g. (recovery, 99.2%) of d-N-p-methoxybenzylphenylpropanolamine hydrochloride having an optical rotation in methanol of +3.3° and a melting point of 186° C.

EXAMPLE 5 a. A mixture of 26.0 g. (0.2 mole) of DL-pantolactone, 43.4 g (0.16 mole) of 1-N-p-methoxybenzylphenylpropanol amine and 300 ml. of water was stirred for 2 hours on a boiling water bath. After being cooled, the reaction mixture was filtered to collect the formed crystals which were in turn washed with water, thereby giving 40.5 g. (yield, 96.6%) of L-pantoic acid 1-N-p-methoxybenzylphenylpropanolamine as crystals having an optical rotation of −10.8° in methanol.

A solution of 38.5 g. of said cyrstals in 55 ml. of a 10% potassium hydroxide aqueous solution was washed three times with 80 ml. of ether. To the aqueous layer was added 15 ml. of a 50% sulfuric acid solution, and the mixture was heated for 30 minutes at 80°C. on a water bath. After being cooled, the mixture was extracted with chloroform continuously overnight and the extract was dried over anhydrous sodium sulfate. The removal therefrom of the solvent gave 10.8 g. (yield, 87.4%) of L-pantolactone as crystals having an optical rotation in water of +49.9° and a melting point of 89° to 90° C.

b. The mother liquid from which said amine salt of L-pantoic acid had been separated was combined with said water washing, and the water was distilled off from said combined mixture under reduced pressure. The resulting residue was dissolved in 65 ml. of a 10% potassium hydroxide aqueous solution, and the resulting solution was washed three times with 80 ml. of ether. The aqueous layer was mixed with 18 ml. of a 50% sulfuric acid solution and the mixture was heated for 30 minutes at 80° C. on a water bath. After being cooled, the mixture was extracted with chloroform continuously overnight and the extract was dried over anhydrous sodium sulfate. The removal of the solvent therefrom and the subsequent recrystallization thereof from a benzene-ligroin mixture gave 11.1 g. (yield, 85.4%) of D-pantolactone as crystals having an optical rotation in water of −50.1° and a melting point of 89 to 90° C.

EXAMPLE 6 a. A solution of 26.0 g. (0.2 mole) of DL-pantolactone in 50 ml. of an aqueous solution containing 8.2 g. of sodium hydroxide was adjusted to pH 7.2 with 10% hydrochloric acid. To this solution was added a solution which was previously obtained by adding 62.5 g. (0.2 mole) of 1-N-o-chlorobenzylphenylpropanolamine hydrochloride to 300 ml. of water and heating the mixture on a water bath to dissolve the hydrochloride in water. After being cooled, the mixture was filtered to collect the formed crystals which were in turn washed with water to give 37.7 g. (yield, 89.0%) of L-pantoic acid 1-N-o-chlorobenzylphenylpropanolamine as crystals having an optical rotation of −16.7° in methanol.

A solution of 35.0 g. of said crystals in 45 ml. of a 10% sodium hydroxide aqueous solution was washed three times with 50 ml. of benzene. The aqueous phase was mixed with 15 ml. of 50% sulfuric acid and heated for 30 minutes at 80° C. on a water bath. After being cooled, the mixture was extracted with chloroform continuously overnight, followed by the drying over anhydrous sodium sulfate and the removal of the chloroform. This gave 9.8 g. (yield, 81.2%) of L-pantolactone as crystals having an optical rotation in water of +49.9° and a melting point of 89° to 90° C.

b. The mother liquid from which said amine salt of L-pantoic acid had been removed and said water washing were combined, and the water was distilled off from the mixture under reduced pressure. The resulting residue was dissolved in 55 ml. of a 10% sodium hydroxide aqueous solution, and the mixture was washed three times with 50 ml. of benzene. To this aqueous layer was added 18 ml. of 50% sulfuric acid, and the mixture was heated for 30 minutes at 80° C. on a water bath, followed by cooling said mixture and extracting it with chloroform continuously overnight. After the extract was dried over anhydrous sodium sulfate, the chloroform was removed and the residue was recrystallized from a mixture of 1,2-dichloropropane and petroleum benzene to give 10.6 g. (yield, 81.5%) of crystalline D-pantolactone having an optical rotation of −50.1° in water and a melting point of 90° to 91° C.

c. A combined mixture of all said benzene phases was treated in the same manner as in Example 4(c) to give 62.0 g. (recovery, 99.2%) of 1-N-o-chlorobenzylphenylpropanolamine hydrochloride having an optical rotation in methanol of −15.2° and a melting point of 195° C.

EXAMPLE 7 a. A solution of 26.0 g. (0.2 mole) of DL-pantolactone in 50 ml. of an aqueous solution containing 8.2 g. of sodium hydroxide was adjusted to pH 7.2 with 10% hydrochloric acid. To this solution was added a solution which had been obtained by adding 35.0 g. (0.12 mole)

of d-N-p-methylbenzylphenylpropanolamine hydrochloride to 60 ml. of methanol while being heated on a water bath. The resulting mixture was left to stand overnight to precipitate out crystals. The crystals were filtered and washed with a 50% methanol solution, thereby giving 36.1 g. (yield, 89.5%) of D-pantoic acid d-N-p-methylbenzylphenylpropanolamine as crystals having an optical rotation of +11.7° in methanol.

A solution of 33.0 g. of said crystals in 45 ml. of a 10% sodium hydroxide aqueous solution was washed three times with 50 ml. of benzene. This aqueous layer was mixed with 20 ml. of concentrated hydrochloric acid and heated for 30 minutes at 80°C. on a water bath. After being cooled, the solution was extracted continuously with chloroform overnight and the chloroform phase was dried over anhydrous sodium sulfate to be followed by distilling off the solvent therefrom, thereby giving 10.0 g. (yield, 84.1%) of D-pantolactone as crystals having an optical rotation of −48.4° in water and a melting point of 88° to 89° C.

b. A combined mixture of the mother liquor from which said amine salt of D-pantoic acid had been separated and said water washing was treated under reduced pressure to distil off the solvent. The resulting residue was dissolved in 55 ml. of a 10% sodium hydroxide aqueous solution and washed three times with 50 ml. of benzene. The aqueous layer was mixed with 30 ml. of concentrated hydrochloric acid to be followed by heating the mixture for 30 minutes at 80° C. on a water bath and cooling it. The resulting solution was then extracted with chloroform continuously overnight, followed by the drying of the organic layer over anhydrous sodium sulfate and removing the solvent therefrom. The resulting residue was then recrystallized from trichlene to give 10.2 g. (yield, 78.5%) of L-pantolactone as crystals which had an optical rotation in water of +47.9° and a melting point of 88° to 89° C.

EXAMPLE 8 a. A solution of 26.0 g. (0.2 mole) of DL-pantolactone in 50 ml. of an aqueous solution containing 8.2 g. of sodium hydroxide was adjusted to pH 7.2 with 10% hydrochloric acid. To this solution was added a solution of 61.2 g. (0.2 mole) of 1-N-(gamma-phenylpropyl)-phenylpropanolamine hydrochloride which had been dissolved in 100 ml. of methanol by heating the mixture on a water bath. After the removal of the solvent from said mixture and the addition thereto of isopropyl alcohol, the precipitated sodium chloride was filtered off and the filtrate was left to stand overnight. The mixture was then filtered and washed with isopropyl alcohol to give 31.3 g. (yield, 75.0%) of L-pantoic acid 1-N-(gamma-phenylpropyl)phenylpropanolamine as crystals. They had an optical rotation of +19.9° in methanol.

A solution of 29.0 g. of said crystals in 45 ml. of a 10% sodium hydroxide aqueous solution was washed three times with 50 ml. of benzene. The aqueous layer was mixed with 20 ml. of concentrated hydrochloric acid and heated for 30 minutes at 80° C. on a water bath, followed by cooling the mixture and then extracting it with chloroform continuously overnight. The chloroform layer was then dried over anhydrous sodium sulfate, and the chloroform was removed to give 8.5 g. (yield, 70.6%) of crystalline L-pantolactone having an optical rotation in water of +48.5° and a melting pont of 88° to 89° C.

What is claimed is:

1. A method of optically resolving DL-pantolactone which comprises reacting DL-pantolactone or its basic salt with an opticaly active N-substituted aminophenylpropanol of the general formula:

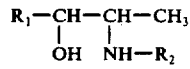

wherein $R_1$ is a phenyl group which may be substituted by a halogen atom, an aliphatic lower alkyl group having from 1 to 4 carbon atoms or an aliphatic lower alkoxy group having a 1 to 4 carbon atom alkyl and $R_2$ is an aralkyl group having from 7 to 10 carbon atoms which may be substituted on the benzene ring by a halogen atom, an aliphatic lower alkyl having from 1 to 4 carbon atoms or an aliphatic lower alkoxy whose alkyl has from 1 to 4 carbon atoms, or a mineral acid addition salt, respectively, separating the resulting diastereomer by the aid of difference in their dissolubility and decomposing the diastereomer into the corresponding antipode.

2. The method of claim 1, wherein said basic salt is sodium or potassium salt.

3. The method of claim 1, wherein said mineral acid addition salt is hydrochloric or sulfuric acid addition salt.

4. The method of claim 1, wherein said optically active N-substituted aminophenylpropanol or its basic salt is used in an amount of at least 0.5 mole with respect to the stoichiometrically equimolar amount.

5. The method of claim 1, wherein said reaction is carried out in the presence of a solvent.

6. The method of claim 5, wherein said solvent is water or a mixture thereof with an aliphatic lower alcohol or an aliphatic lower ketone.

7. The method of claim 1, wherein said diastereomer is separated into the corresponding sparingly soluble diastereomer and easily soluble diastereomer by the aid of difference in dissolubility.

8. The method of claim 7, wherein said diastereomer is decomposed with an alkali or a mineral acid.

9. The method of claim 8, wherein said alkali is sodium or potassium hydroxide.

10. The method of claim 8, wherein said mineral acid is hydrochloric acid or sulfuric acid.

11. The method of claim 7, wherein said sparingly soluble diastereomer is treated with said alkali or mineral acid and then with a solvent incompatible with water.

12. The method of claim 11, wherein said solvent is benzene or ether.

13. The method of claim 1, wherein said optically active N-substituted aminophenylpropanol is recovered from the mixture from which said antipode is separated.

* * * * *